(12) United States Patent
Marchionni et al.

(10) Patent No.: US 6,896,996 B2
(45) Date of Patent: *May 24, 2005

(54) PERFLUOROPOLYETHER ADDITIVES FOR ELECTROCHEMICAL APPLICATIONS

(75) Inventors: Giuseppe Marchionni, Milan (IT); Alberto Zompatori, Bologna (IT); Alba Chittofrati, Novara (IT)

(73) Assignee: Austmont S.p.A., Milan (IT)

( * ) Notice: Subject to any disclaimer, the term of this patent is extended or adjusted under 35 U.S.C. 154(b) by 417 days.

This patent is subject to a terminal disclaimer.

(21) Appl. No.: 10/028,310

(22) Filed: Dec. 28, 2001

(65) Prior Publication Data

US 2002/0127475 A1 Sep. 12, 2002

(30) Foreign Application Priority Data

Jan. 3, 2001 (IT) .................................... MI2001A0008

(51) Int. Cl.$^7$ ................................................. H01M 6/16
(52) U.S. Cl. ...................... 429/324; 429/199; 568/579; 525/326.2
(58) Field of Search ................................ 429/324, 199; 568/579; 525/326.2

(56) References Cited

U.S. PATENT DOCUMENTS

| | | | |
|---|---|---|---|
| 5,142,842 A | | 9/1992 | Schirmer |
| 5,258,110 A | | 11/1993 | Sianesi et al. |
| 5,488,181 A | | 1/1996 | Marchionni et al. |
| 5,882,810 A | * | 3/1999 | Mussell et al. ............... 429/33 |
| 6,403,539 B1 | * | 6/2002 | Marchionni et al. ......... 508/406 |

FOREIGN PATENT DOCUMENTS

| | | |
|---|---|---|
| EP | 0 244 839 A2 | 11/1987 |
| WO | WO 98/18627 | 5/1998 |
| WO | WO 99/30381 | 6/1999 |

OTHER PUBLICATIONS

Huh et al, "A Rigorous Theory of Ring Tensiometry", Colloid & Polymer Sci., vol. 253, 1975, pp 566–580.
Morra et al, "Knowledge About Polymer Surfaces from Contact Angle Measurements", Advances in Colloid and Interface Science, vol. 32, 1990, pp 79–116.
Johnson et al, "Dynamic Contact Angles and Contact Angle Hysteresis", Journal of Colloid and Interface Science, vol. 62, No. 2, Nov. 1977, pp 205–212.
Lamont et al, "Organized Structure of Lithium Perfluorooctanesulfonate at the Graphite—Solution Interface", Journal of Colloid and Interface Science, vol. 191, 1997, pp 303–311.

* cited by examiner

*Primary Examiner*—Patrick Joseph Ryan
*Assistant Examiner*—Julian Mercado
(74) *Attorney, Agent, or Firm*—Arent Fox PLLC

(57) ABSTRACT

Electrolytic compositions comprising a perfluoropolyether additive of formula (I):

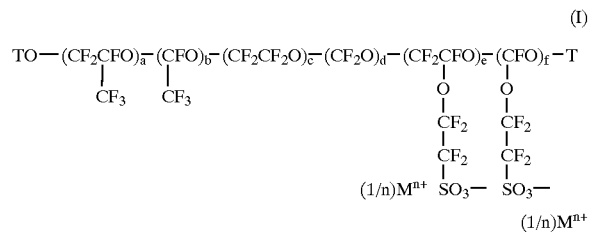

wherein:
 d, e, f are integers; a, b, c can be zero or integers; being a+b+c+d+e+f such that the number average molecular weight ranges from 500 to $5 \times 10^5$;
 T are end groups —$CF_2X$ (X=F, $CF_3$, Cl), —$C_3F_7$, —CF($CF_3$)COO$^-$(1/n)M$^{n+}$, —$CF_2$COO$^-$(1/n) M$^{n+}$, —$CF_2$C(O(1/n)M$^{n+}$)$_2$CF$_3$;
 M$^{n-}$ is a cation having valence n=1–4.

21 Claims, No Drawings

PERFLUOROPOLYETHER ADDITIVES FOR ELECTROCHEMICAL APPLICATIONS

The present invention relates to additives which allow to improve the wettability of the components of an electrochemical system.

Specifically, the invention relates to perfluoropolyether additives having perfluoroalkansulphonated groups, which used in electrolytic compositions, allow an improved wettability of electrodes and separatory membranes of electrochemical systems, for example lithium batteries, maintaining a high conductivity.

It is known in the prior art that the electrolytes for electrochemical systems working at high voltage, for example lithium batteries, are prepared by dissolving one or more conductive salts in one or more aprotic dipolar solvents to obtain an electrolytic solution. The obtained solution swell the polymer membranes which separate the electrodes of the electrolytic cell assuring the system conductivity. The more effective the electrolyte the more the wettability of components of the electrochemical cell, for example electrodes and separatory membrane.

It is known that the wettability of a liquid towards a substratum depends on the surface tension of the liquid with respect to the solid. To obtain the wettability of the separatory polymer membrane, the electrolyte solution must have a surface tension at least equal to that of the membrane and preferably lower to increase the wettability efficacy and wetting homogeneity. Generally, the electrolytic solutions used in the prior art show a high surface tension and a high viscosity, which prevent an effective wettability of the separatory membrane and of the electrodes. Besides, the small sizes and the compact form of the batteries make more difficult the membrane wettability.

Therefore one tries to have available electrolytic solutions which even maintaining a good conductivity, have a lower surface tension with respect to the separatory membrane to have better wetting properties. The improvement of the wetting properties of the electrolyte implies the further advantage to be able to use electrodes having a lower porosity and therefore a higher energy density.

Special techniques, such for example processes under vacuum or under pressure, can be used to make more effective the wettability of the cell components from the electrolyte. However, these techniques undesirably complicate the impregnation process and lengthen the times required for the achievement of the electrolytic cell.

Another way to decrease the surface tension of electrolytic solutions and therefore to increase their wetting capability is the addition of surfactants to the electrolytic solutions. However, the surfactants used in the prior art have negative effects as regards the electrochemical cell performances, since they decrease the electrolyte chemical and thermal stability or reduce the cell ionic conductivity.

Patent application WO 99/30381 relates to perfluorinated imide salts which, when used in an electrolytic solution, allow to improve the wetting properties thereof towards the electrodes and the separatory membrane. Tests carried out by the Applicant, see the comparative Examples, show that the imide salt $(C_4F_9SO_2)_2N^-Li^+$ exemplified in WO 99/30381, when added to an electrolytic solution, produces a lowering of the surface tension of the solution. However, the reduction of the surface tension is just sufficient to guarantee the wettability of the separatory membrane, since the surface tension of the resulting solution is very similar to the critical surface tension of the substratum. Besides, the synthesis process of bis(perfluoroalkylsulphonyl)imides described in said application is complex since it requires various synthesis steps. The obtained products are therefore very expensive.

The need was felt to have available cheaper additives able to increase the wetting properties of electrolytic solutions towards electrodes and separatory membranes, thus making quicker and more effective the preparation process of electrochemical cells.

The Applicant has surprisingly and unexpectedly found an additive capable to improve the wetting properties of the electrolytic solutions towards the components of an electrochemical cell, without negatively affecting the chemical and thermal stability of the cell and its performances in conductivity terms.

An object of the invention are electrolytic compositions comprising a perfluoropolyether additive of formula (I):

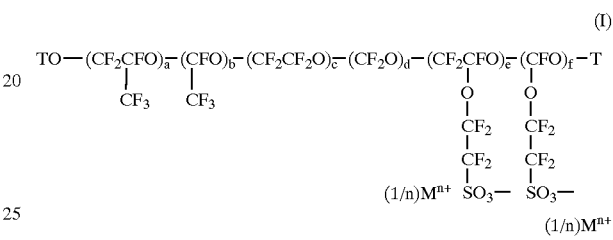

wherein:

d, e, f are integers; a, b, c can be zero or integers; said units are statistically distributed along the chain, being a+b+c+d+e+f such that the number average molecular weight ranges from 500 to $5 \times 10^5$, preferably from 1,000 to 50,000;

T are end groups selected from —$CF_2X$ (X=F, $CF_3$, Cl), —$C_3F_7$, —$CF(CF_3)COO^-$ $(1/n)M^{n+}$, —$CF_2COO^-$ $(1/n)M^{n+}$, —$CF_2C(O(1/n)M^{n+})_2CF_3$;

$M^{n+}$ is a cation having valence n=1–4; alkaline metal cations (for example $Li^+$, $Na^+$, $K^+$, $Cs^+$); alkaline-earth metal cations (for example $Mg^{2+}$, $Ca^{2+}$, $Sr^{2+}$, $Ba^{2+}$); metal cations of the group IIIA (for example $Al^{3+}$); transition metal cations (for example $Fe^{2+}$, $Fe^{3+}$, $Zn^{2+}$, $Ti^{4+}$, $Cu^{2+}$); tetraalkylammonium $NR_4^+$ cations, trialkylammonium $NR_3^+$ cations, wherein R is selected from H, a linear or branched when possible $C_1$–$C_4$ lower alkyl can be mentioned.

Preferably as additives of the present invention monovalent cations (n=1), more preferably M=Li are used. The selection of the cation and of the molecular weight of the perfluoro-polyether additive must be such to assure the stability of the electrolytic solution.

The electrolytic compositions of the invention, besides the additive of formula (I), comprise:
one or more aprotic polar solvents;
a conductive salt having the function to assure the ionic conductivity inside the cell.

As conductive salt to be used in the electrolytic composition of the invention, salts commonly employed in electrochemical systems can be used. Salts can be mentioned wherein the cation is selected from the group comprising $H^+$, alkaline, alkaline-earth metals, trivalent metals, tetraalkylammonium and the anion is selected from: $PF_6^-$, $ClO_4^-$, $AsF_6^-$, $BF_4^-$, $(R_{f1}SO_2)(R_{f2}SO_2)N^-$, $R_{f'}SO_3^-$ wherein $R_{f1}$, $R_{f2}$, $R_{f'}$ are independently selected from $C_1$–$C_4$ perfluoroalkyl groups optionally containing heteroatoms. $PF_6^-$, $ClO_4^-$ are preferably used.

The solvents used to dissolve the conductive salt and the perfluoropolyether additive of the invention are aprotic polar solvents having a limited content of water, preferably lower than 50 ppm, such as for example 1,2-dimethoxyethane, 1,2-diethoxyethane, 1,3-dioxolane, 2-methyl-1,3-dioxolane, 4-methyl-1,3-dioxolane, tetrahydrofuran, 2-methyltetrahydrofuran, 1,4-dioxane, diethylcarbonate, propylencarbonate, ethylencarbonate, dimethylcarbonate, N,N-dimethyformamide, dimethysulphoxide. Preferably ester carbonates are used as aprotic polar solvents. It has been found by the Applicant that the additives of the invention, specifically those with M monovalent, are particularly soluble in the above solvents.

Generally, the concentration of conductive salt in the electrolytic solution is higher than 0.5 moles/liter, preferably in the range 0.5–2 moles/liter, the concentration of the perfluoropolyether additive is higher than 10 meq/liter (calculated as cation $M^{n+}$), preferably in the range 10 meq/liter-500 meq/liter.

It is known that in electrochemical cells the ionic species are at least partially dissolved or dispersed in a matrix material having the function to separate the anode and the cathode avoiding short circuits. The matrix material can be in the form of solid, liquid polymer, gel or porous membrane. The solid polymer materials, optionally crosslinked, suitable to be used as matrix in electrochemical cells are selected from polyethylenoxide, polyesters, polyacrylates, polyvinilydenfluoride, polyacrylonitrile, having a water content preferably lower than 50 ppm. Usually, as matrix material in the form of porous solid membranes, microporous polymers are used, such for example polyethylene, polypropylene having a surface tension generally in the range 28–35 mN/m (dyne/cm).

The additives of the invention allow to decrease the surface tension of the electrolytic solution and to increase its wetting properties towards electrodes and separatory membranes of the electrochemical cell.

The additives of the invention show a high thermal stability, even at temperatures of the order of 300° C. and show a high chemical stability in the use conditions of the electrochemical cells. The perfluoropolyether compounds of the invention, besides increasing the wetting properties of the electrolytic solution, contribute to the system charge transport, and therefore to its conductivity, by their dissociable cations (see the Examples).

Another advantage of the invention resides in that the surface tension lowering conferred by the additives of the invention allows the use of solvents having a high viscosity and surface tension, such as for example propylencarbonate. In fact, in absence of additives, such as the products of the invention, which lower the surface tension of the solution, said solvents must be used in admixture with other solvents (for example dimethoxyethane, dimethylcarbonate, etc.) which have the further effect to lower the dielectric constant of the medium, worsening the electrochemical system efficiency. Therefore, the additives of the invention allow to increase the system conductivity, and the consequent battery functionality.

The perfluoropolyether additives of the present invention contain one or more perfluorinated units of the type $-(CF_2CF(CF_3)O)-$, $-(CF(CF_3)O)-$, $-(CF_2CF_2O)-$, $-(CF_2O)-$, $-(CF_2CF(OCF_2CF_2SO_3^-(1/n)M^{n+})O)-$, $-(CF(OCF_2CF_2SO_3^-(1/n)M^{n+})O)-$—statistically distributed along the chain and in an amount variable depending on the operating process conditions mentioned below.

The perfluoropolyether additives of the invention are obtainable by conversion of the fluorosulphonyl groups $-SO_2F$ into $-SO_3M$ groups carried out on the homopolymers of the monomer $CF_2=CFOCF_2CF_2SO_2F$ (perfluoro 3-oxa 5-fluorosulphonyl 1-pentene), or on the copolymers of said monomer with perfluoroolefins. The perfluoroolefins used as comonomers of $CF_2=CFOCF_2CF_2SO_2F$ are preferably tetrafluoroethylene and/or perfluoropropene.

When tetrafluoroethylene is used as comonomer of the perfluoro 3-oxa 5-fluorosulphonyl 1-pentene ($CF_2=CFOCF_2CF_2SO_2F$), perfluoropolyether copolymers having structure (II) are obtained:

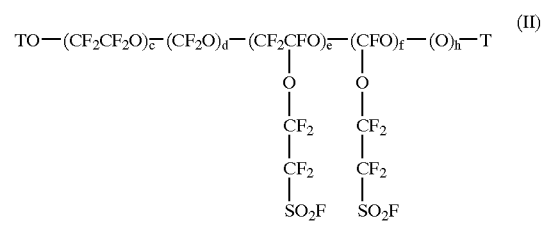

wherein: T are end groups selected from $-CF_2X$ (X=F, $CF_3$, Cl), $-COF$, $-CF_2COF$;

c, d, e, f, h are integers with the proviso that c cannot be equal to 0.

When hexafluoropropene ($CF_2=CF-CF_3$) is used as comonomer, perfluoropolyether copolymers of structure (III) are obtained:

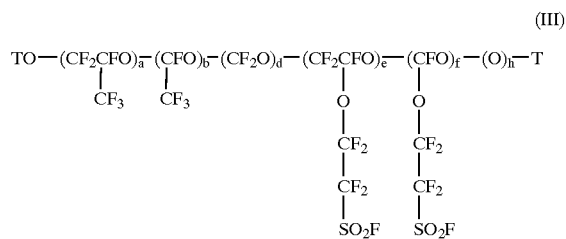

wherein: T are end groups selected from $-CF_2X$ (X=F, $CF_3$), $-C_3F_7$, $-COF$, $-CF_2COF$, $-CF(CF_3)$ COF, $-CF_2COCF_3$; a, b, d, e, f, h have the above meaning with the proviso that a, b cannot be 0.

When $CF_2=CFOCF_2CF_2SO_2F$ is copolymerized with a mixture of tetrafluoroethylene and perfluoropropene, perfluoropolyether copolymers of formula (IV) are obtained:

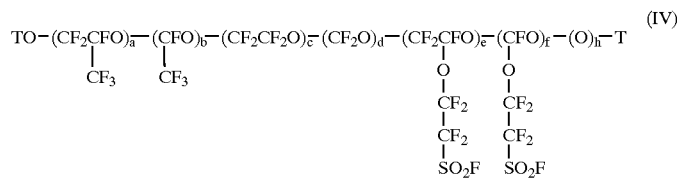

wherein: T are end groups selected from —CF$_2$X (X=F, CF$_3$, Cl), —C$_3$F$_7$, —COF, —CF(CF$_3$)COF, —CF$_2$COF, —CF$_2$COCF$_3$;
a, b, c, d, e, f, h are integers.

When CF$_2$=CFOCF$_2$CF$_2$SO$_2$F is homopolymerized, a PFPE of structure (V) is obtained:

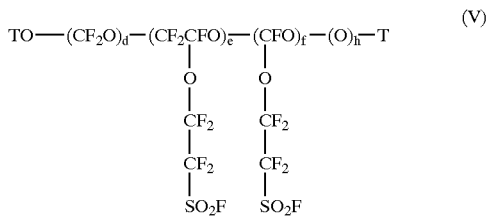

wherein: T are end groups selected from —CF$_2$X (X=F, CF$_3$,Cl), —COF, —CF$_2$COF, —CF$_2$CF$_2$SO$_2$F;
d, e, f, h have the above defined meaning.

In the homopolymer case, there is the maximum concentration of sulphonic groups, not obtainable with any other synthesis method so far known. The high number of sulphonic groups allows, the molarity being equal, to use an amount by weight of the additive of the invention lower than that of the compounds of the prior art. This represents an advantage since it allows to reduce the used amount and therefore the related costs.

The additives of formula (I) of the invention are obtainable starting from the above homopolymers or copolymers having the —SO$_2$F function. These homopolymers or copolymers are obtainable by a photooxidation process of the monomers, i.e. a (co)polymerization process in the presence of oxygen which utilizes the action of ultraviolet radiations. An alternative process is the polymerization of monomers without the use of ultraviolet radiations and uses compounds having the function of polymerization initiators. Also a mixed process which uses UV radiations and polymerization initiators as defined below can be used.

In the former case the monomer perfluoro 3-oxa 5-fluorosulphonyl 1-pentene (CF$_2$=CFOCF$_2$CF$_2$SO$_2$F), optionally perfluorinated olefins, are contemporaneously fed with an O$_2$ flow in a liquid reaction mixture formed by a solvent selected from chlorofluorocarbons (CFC), hydrochlorofluorocarbons (HCFC), hydrofluorocarbons (HFC), fluoroethers (FE), hydrofluoroethers (HFE), fluorocarbons (FC) or mixtures thereof. In the case of copolymerization with hexafluoropropene (HFP) one usually operates in absence of solvent. During the polymerization, the liquid reaction medium is maintained at a temperature in the range from −100° to +50° C., preferably from −90° to −30° C., and irradiated with ultraviolet radiation having wave length in the range 2,000–6,000 A°.

In the latter case the monomer CF$_2$=CFOCF$_2$CF$_2$SO$_2$F, optionally perfluorinated olefins, are contemporaneously fed with an O$_2$ flow to a liquid reaction medium formed by a solvent selected from the above compounds. In the liquid reaction medium, maintained at a temperature in the range from −100° to +50° C., preferably from −90° to −30° C., a gaseous or liquid flow of one or more compounds having one or more bonds F-Q wherein Q is selected between fluorine and oxygen is fed; when Q is oxygen, the initiator is an organic compound containing one or more fluoroxy groups. Commonly the initiator is a FOR$_f$ compound wherein R$_f$ is a perfluoroalkyl radical having from 1 to 3 carbon atoms; or it is a compound of the type FOCF$_2$OF, FO—(RO)$_s$—F, R$_f$—(RO)$_s$—F with R perfluoroalkylene radical of the type —CF$_2$—, —CF$_2$CF$_2$—, —CF$_2$CF(CF$_3$)—, wherein s is in the range 1–100. Said initiators are described in U.S. Pat. No. 5,142,842, U.S. Pat. No. 5,258,110, U.S. Pat. No. 5,488,181. The initiator flow-rate is adjusted so that the molar ratio between the initiator and the monomers in the reaction medium is in the range 0.0001–0.1.

In the mixed process, it is used the process of the latter case in the presence of UV radiations.

In the processes of the invention oxygen is fed into the reactor, the partial oxygen pressure is generally in the range 0.01–15 atmospheres; the concentration of the CF$_2$=CFOCF$_2$CF$_2$SO$_2$F monomer is generally comprised between 0.001 mole/liter and its molar concentration at the pure state. By molar concentration at the pure state, it is meant that the polymerization can be carried out in the presence of the sulphonyl monomer at the liquid state, or the maximum concentration of said monomer in the above indicated used solvent. The skilled is easily able to determine said maximum concentration.

The reaction can be carried out in batch or in a continuous way, continuously drawing from the reactor an aliquot of the liquid phase, subjecting it to distillation, recycling the solvent, if any, and the unreacted monomers and recovering the reaction product.

In the case of copolymers, the frequency of the sulphonylfluoride group —CF(OCF$_2$CF$_2$SO$_2$F)— in the chain is proportional to the ratio perfluoroalkylsulphonylvinylether/olefins in the reaction mixture and it can range from 1 to 99% of the total units of the perfluoropolyether.

From the above described polymerization techniques perfluoropolyethers containing in the chain peroxidic groups are obtained. The peroxidic bond scission brings to the formation of functionalized end groups, making available perfluoropolyether structures having mono and bifunctional end groups of the —COR (R=F, —OH, —OCH$_3$, —OC$_2$H$_5$, —OC$_3$H$_7$) type or of the —OCF$_2$Y (Y=Br, I) type and containing along the backbone pendent sulphonic groups. This is a further advantage of the products of the invention, since polycondensation polymers can be prepared by using the aforesaid end groups. Said scission processes are described in EP 244,839 and EP 939,700 in the name of the Applicant, herein incorporated by reference, wherein also the obtainment of the functional compound is indicated.

To obtain non peroxidic products without chain scission the peroxidic perfluoropolyethers are subjected to a thermal treatment at temperatures generally comprised between 150° C. and 250° C., or to a photochemical treatment at temperatures generally comprised between −40° C. and +150° C. in the presence of UV radiations having wave length between 2,000 and 6,000 A° and in the presence of an optional solvent. By fluorination of the so obtained products, products having formulas (II), (III), (IV) and (V) are obtained wherein h=0 and the end groups T are CF$_2$X or C$_3$F$_7$ as above indicated.

The additives of the invention of formula (I) are obtained by conversion of the fluorosulphonyl groups —OCF$_2$CF$_2$SO$_2$F of the perfluoropolyethers not containing peroxidic oxygen. The conversion of the fluorosulphonyl groups is carried out by hydrolysis using an excess of M metals hydroxides and then carbonating the excess of unreacted hydroxides by bubbling CO$_2$ in the aqueous solution. The insoluble inorganic salts obtained from the reaction are removed by evaporation of the water at reduced pressure and repeated hot washings with absolute alcohol and subsequent filtration of the insoluble residue. The additives of the invention are isolated by evaporation at reduced pressure of the ethanol.

The present invention will be better illustrated by the following Examples, which have a merely indicative but not limitative purpose of the scope of the invention itself.

EXAMPLES

Characterization

Surface Tension

The surface tensions of the electrolytic solutions have been measured by the De Noüy method according to ASTM D1331-89. The method determines, by microbalance, the maximum exertable force F in the extraction of a Pt ring from the liquid, without complete detachment and breaking of the surface film. The surface tension is equivalent to the force which opposes the ring detachment and it can be expressed in mN/m both as force for length unit and as work for surface unit. The surface tension value is deduced from F by tabulated corrective factors which include the ring geometric parameters and the liquid density. All the measurements have been performed at 25° C. with the KSV Sigma 70 equipment, using the corrective factor of Huh-Mason (as described in Colloid Polym. Sci., 253 (1975) 566), repeating the measurements in the time up to a constant value for at least 5 consecutive measurements.

Dynamic Contact Angle

The wetting properties of a liquid towards a solid substratum depend on the contact angle θ, defined by the intersection of the planes tangent to the liquid the liquid and solid surfaces. The condition of complete wettability corresponds to θ equal to zero, while θ equal to 180° corresponds to zero wettability (ideally spherical drop of liquid on the substratum in equilibrium conditions). Between the techniques of static and dynamic measurements known in the prior art, the same equipment KSV Sigma 70, used also as tensiometer, has been used for the dynamic contact angle measurement. With this technique, a specimen of the substratum is connected to the microbalance and the variation of the force is determined in connection with the position during immersion and emersion cycles of the solid from the liquid, recording tensiograms from which, for each cycle, both the advancing contact angle ($\theta_{adv}$) and the recession angle ($\theta_{rec}$) are deduced. The difference between $\theta_{adv}$ and $\theta_{rec}$ is known in the literature (see for example Adv. Colloid Interface Sci., 32 (1990) 79 and J. Colloid Interface Sci., 62 (1977) 205) as thermodynamic hysteresis and it is associated to several variables among which heterogeneity and roughness of the substratum. The difference of $\theta_{adv}$ among subsequent cycles is known as kinetic hysteresis and it is associated to the evolution of the surface characteristics in the time and used for the study of the progressive adsorption on the substratum of surfactant species in solution (see for example J. Colloid Interface Sci., 191 (1997) 303).

All the measurements have been performed at 25° C., at a dipping rate of the substratum of 6 mm/min. As substratum moulded plates of low density polyethylene (LDPE) have been used, having a value of critical surface tension $\gamma_{cr}$ of 30±1 mN/m, using contact angle measurements of the substratum towards pure liquids having a known surface tension.

Viscosity

The Viscosities have been measured at 25° C. by Cannon-Fenske viscometer according to the ASTM D 445 method.

Density

The Density measurements have been carried out by the PAAR DMA 48 densimeter at 25° C.

Specific Conductivity

The Specific Conductivity κ measurements have been carried out by an AMEL mod. 360 conductimeter (measurement frequency 1 KHz at κ>100 μS/cm and 40 Hz at lower κ), with Pt. cell having a constant of 0.995 cm.

The model system used to evaluate the measurement conditions in the mixture ethylencarbonate/propylencarbonate (EC/PC) 1:1 is the salt $CF_3(CF_2)_6 CF_2SO_3^-Li^+$. Within the solubility limits of this salt in the solvent, linearity between conductivity and concentration has been obtained.

Each specimen has been put in a thermostated glass cell at 25±0.5° C. under magnetic stirring, bubbling $N_2$, anhydrified with $CaCl_2$ and saturated in the same anhydrified solvent mixture for 20 minutes. Subsequently, each solution has been maintained under inert atmosphere, following the conductivity variation thereof in the time up to a constant value. The difference between the initial value and that of the equilibrium was always around 1% of the equilibrium value. The specific conductivity values reported in the Examples refer at least 3–4 measurements with a deviation within ±0,5%.

Example 1

Example 1A

Preparation of the Peroxidic Homopolymer PFPE

In a cylindrical glass reactor (1200 ml volume and optical path of 2 cm) equipped with an internal coaxial quartz sheath and equipped furthermore with a bubbling pipe for the gas introduction, of a sheath with thermocouple for the measurement of the internal temperature and of a condenser maintained at the temperature of −80° C., 1160 g of $CF_2=CFOCF_2—CF_2SO_2F$ and 820 g of $CF_2Cl_2$ are introduced at the temperature of −62° C. Through the bubbling pipe 13 1/h of $O_2$ are bubbled into the reactor. By a refrigerant bath placed outside the reactor the temperature of the reacting liquid phase is maintained at −62° C. for the whole test.

After having introduced in the quartz sheath a UV ray lamp of the HANAU TQ 150 type (which emits 47 watt of UV radiation having wave length in the range 2,000 and 3,000 Å) it is turned on and the irradiation and the oxygen feeding are continued for 15 hours. The UV lamp heat is controlled by a closed cycle cooling system. After 15 hours of irradiation, the lamp is turned off and the $CF_2Cl_2$ is recovered by evaporation at room temperature. 1,076 g of a colourless oily residue are obtained. Said product has (iodometric titration) an active (peroxidic) oxygen content equal to 0.35% by weight.

The so obtained product is placed in a reactor equipped with stirrer at the temperature of 100° C. under nitrogen flow, recovering in a trap cooled at −80° C. the distillable products. In the reactor 481 g of product remain which have (iodometric titration) an active (peroxidic) oxygen content equal to 0.3% by weight and by NMR $^{19}F$ analysis it results to have the following structure:

wherein T'=—$CF_2Cl(1\%)$, —$CF_3(\%)$, —$CF_2COF(30\%)$, —COF(68%); d=26.6; e=23.5; f=17.2; h=1.2. The average molecular weight is 12,900.

Removal of the Peroxidic Groups

In a 500 ml glass reactor equipped with stirrer, thermometer and condenser, 480 g of the above obtained polymer product are introduced. The temperature is brought to 240° C. in 1 hour; the reactor is maintained at the temperature of 240° C. for further 2 hours. At the end of the reaction 460 g of product are recovered which have (iodometric Nitration) an active oxygen content zero and at the NMR $^{19}F$ analysis it results to be formed by polyether chains of the type:

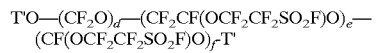

wherein T'=—$CF_2Cl(1\%)$, —$CF_3(1\%)$, —$CF_2COF(60\%)$, —COF(38%); d=10.3; e=9.1 and f=8.8.

Therefore an average molecular weight of 5,600 is calculated.

Distillation 452 g of the above obtained product are distilled at the pressure of $2.4*10^{-2}$ mbar reaching a maximum temperature in the reactor of 240° C. 126 g of distilled polymer are obtained. The structure of the product determined by NMR $^{19}$F results:

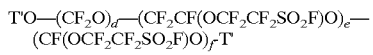

wherein T'=—$CF_3$, —$CF_2COF'$, —$CF_2Cl$; d=1.4; e=3.5; f=4.1.

Therefore an average molecular weight of 2,330 is calculated with an equivalent weight of 288.

The residue recoverd in the reactor, 271 g, analyzed by NMR $^{19}$F has the following structure:

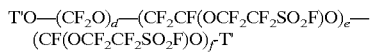

wherein T'=—$CF_3$, —$CF_2COF$, —$CF_2Cl$; d=14.1; e=11.4; f=10.8.

Therefore an average molecular weight of 7,130 is calculated with an equivalent weight of 320.

Conversion of the —$SO_2F$ groups into —$SO_3M$ groups

Subsequently, starting from the obtained products, a conversion of the fluorosulphonyl groups —$OCF_2CF_2SO_2F$ into the corresponding —$OCF_2CF_2SO_3Li$ groups is carried out, obtaining a PFPE lithium sulphonate, the additive of the invention. One operates as follows:

60 grams of PFPE having a molecular weight of 2,330, equal to 188 mmoles of —$SO_2F$, are added, under stirring and at the temperature of 80° C., to an aqueous solution containing an excess of LiOH (25.5 grams, equal to 606 mmoles, in 600 ml of distilled $H_2O$); when the addition is ended in about 30 minutes, the solution becomes turbid due to the LiF formation. One continues to heat under stirring for 5 hours, then the reaction mixture is brought to the room temperature and the unreacted LiOH is carbonated by bubbling carbon dioxide into the solution, until the pH is lower than 7.

The water is evaporated at reduced pressure, a hot washing is carried out with absolute alcohol and the mixture is filtered on porous septum, thus removing the inorganic salts (lithium carbonate and lithium fluoride) insoluble in ethanol. This operation is repeated twice, then the ethanol is evaporated under reduced pressure and 50 grams of PFPE-lithium sulphonate are obtained, with a yield equal to 83%.

The lithium content analysis, carried out by the Inductively Coupled Plasma (ICP) technique, shows a total conversion of the —$SO_2F$ groups of the perfluoropolyether to —$SO_3^{(-)}Li^{(+)}$ and of the end groups —COF to —$COO^-Li^+$.

Example 1B

The same salification procedure described in Example 1A is applied to the PFPE having MW=7,130. A PFPE-lithium sulphonate is obtained which has been characterized by thermogravimetric analysis to determine the thermal stability thereof. The thermogravimetry has been carried out in nitrogen with a temperature gradient of 10° C./min from 30° C. to 700° C. A weight loss of 1.5% at 150° C., of 6% at 250° C., of 20% at 300° C. is determined. These data show that the product has a very good thermal stability and is suitable to be used since the utilization temperatures of the electrochemical cells are generally lower than 150° C.

The Differential Scanning Calorimetry identifies the Tg (On-set) of the PFPE-lithium sulphonate at −37° C.

Example 2

The wetting properties of the additive of the invention towards moulded plates of low density polyethylene (LDPE) having the characteristics mentioned in the characterization part "dynamic contact angle" are evaluated.

The PFPE-lithium sulphonate is used, obtained as described in Example 1A and having EW=288 and $MW_n$=2,330. The PFPE-lithium sulphonate is dissolved in concentration 1 N in a mixture of ethylencarbonate/propylencarbonate EC/PC (50/50 by weight). Then the polyethylene plate is dipped into the prepared solution.

The data relating to subsequent immersion and emersion cycles of the plate are shown in Table 1, wherein the measures of the advancing dynamic contact angle ($\theta_{adv}$) and of the recession angle ($\theta_{rec}$) are reported.

The surface tension value of the PFPE-lithium sulphonate solution in EC/PC is reported in Table 2.

Example 3 (Comparative)

The wetting capability of the imide salt of formula $(C_4F_9SO_2)_2N^{(-)}Li^{(+)}$ obtained according to the method described in the patent application WO99/30,381 is evaluated, towards moulded plates of low density polyethylene (LDPE) of Example 2.

Said imide salt is dissolved in concentration 1 N in an EC/PC mixture 50/50 by weight. Then the polyethylene plate is dipped into the prepared solution.

The data relating to subsequent immersion and emersion cycles of the plate are shown in Table 1, wherein the measures of the advancing dynamic contact angle ($\theta_{adv}$) and of the recession angle ($\theta_{rec}$) are reported.

The surface tension value of the imide salt solution in EC/PC is reported in Table 2.

TABLE 1

| Cycle Number | EXAMPLE 2 | | EXAMPLE 3 (Comp.) | |
|---|---|---|---|---|
| | ($\theta_{adv}$) | ($\theta_{rec}$) | ($\theta_{adv}$) | ($\theta_{rec}$) |
| 1 | 46 | <5 | 65 | <10 |
| 2 | <5 | <5 | 64 | 22 |
| 3 | <5 | <5 | 65 | 25 |
| 4 | <5 | <5 | 67 | 25 |

TABLE 2

| | Surface Tension (mNm$^{-1}$) |
|---|---|
| Example 2 | 21 |
| Example 3 (Comp.) | 31 |

Table 1 points out how in the case of the solution containing the additive PFPE-lithium sulphonate of the invention, already at the first cycle, clearly lower dynamic contact angles are obtained compared with those of the solution containing the imide salt. This means that the solution of Example 2 wets more quickly and more effectively the surface of the polyethylene plate with respect to the solution of Example 3.

Besides, as regards the solution of Example 2, the difference between the first $\theta_{adv}$ and all the other measured angles, together with the absence of hysteresis verified in the subsequent cycles, show the capability of the additive PFPE-lithium sulphonate to permanently modify the substratum surface, making it solvophilic.

From the results of Example 3, wherein hysteresis phenomena are evident also in the cycles following the first one, one concludes that the imide salt additive is unable to permanently modify the substratum surface.

Table 2 points out how the surface tension of the solution 1N of the imide salt is comparable to the critical surface tension of the polyethylene $\gamma_{cr}$=29–31 mN/m. The solution 1N of PFPE-lithium sulphonate having a $\gamma$ clearly lower than the $\gamma_{cr}$ of the polyethylene, is able to wet more quickly and more effectively the polyethylene substratum with respect to the compound of the prior art.

Example 4

The wetting properties conferred by the perfluoropolyether additive of the invention are tested in an electrolytic solution containing as conductive salt $Li^{(+)}PF_6^{(-)}$ (high purity, battery grade) purchased by Aldrich Chimica, Division of the Sigma-Aldrich S.r.l.

A solution 1 N of $LiPF_6$ in propylencarbonate is prepared (solution 1).

A second solution is prepared by adding to the solution 1 the imide salt of formula $(C_4F_9SO_2)_2N^{(-)}Li^{(+)}$ in concentration 0.1 N (solution 2).

A third solution is prepared by adding to the solution 1 the PFPE-lithium sulphonate (EW=288) prepared according to Example 1 and in concentrtion 0.1 N (solution 3).

Solution 1: solution 1N of $LiPF_6$ in PC;
Solution 2: solution 1N of $LiPF_6$ and 0.1N of $(C_4F_9SO_2)_2N^{(-)}Li^{(+)}$ in PC;
Solution 3: solution 1N of $LiPF_6$ and 0.1N PFPE-lithium sulphonate (EW=288) in PC.

The values of the surface tension $\gamma$, viscosity $\eta$ and density $\rho$ of the obtained solutions have been measured.

TABLE 3

| Solution | $\nu$ (mNm$^{-1}$) | $\eta$ (cst) | $\rho$ (g/ml) |
|---|---|---|---|
| 1 | 41.1 | 5.69 | 1.2798 |
| 2 (Comp.) | 33.0 | 7.51 | 1.3001 |
| 3 | 28.4 | 7.05 | 1.2890 |

Table 3 shows that the PFPE-lithium sulphonate of the invention meaningfully decreases the surface tension of the solution 1N of $LiPF_6$, in an extent greater than the imide salt $(C_4F_9SO_2)_2N^{(-)}Li^{(+)}$, the concentration being equal. The data show furthermore that the solution 3 of the invention has lower viscosity and density with respect to the electrolytic solution containing the imide salt.

Example 5

Different solutions of the perfluoropolyether additives of the invention in a mixture EC/PC 1:1 by weight are prepared:

Solution 1: solution 1N of PFPE-lithium sulphonate (EW=288, $M_n$=2,330) in EC/PC.
Solution 2: solution 1N of PFPE-lithium sulphonate (EW=320, $M_n$=7,130) in EC/PC.
Solution 3: soluzione 0.5N of PFPE-lithium sulphonate EW=320, $M_n$=7,130) in EC/PC.
Solution 4: mixture of solvents EC/PC without additive.

The specific conductivity $\kappa$ of the prepared solutions is measured at 25° C. The values are reported in Table 4.

TABLE 4

| Solution | Concentration (N) | $\kappa$ (mS/cm) |
|---|---|---|
| 1 | 1 | 0.871 |
| 2 | 1 | 0.817 |
| 3 | 0.5 | 0.929 |
| 4 EC/PC (1:1) | — | 0.060 |

The specific conductivity values reported in Table 4 show how the PFPE-Li sulphonates of the invention, besides conferring wetting properties, behave as electrolytes, increasing the specific conductivity of the mixture of solvents.

Example 6

The specific conductivity $\kappa$ has ben measured at 25° C. of the following electrolytic solutions containing the PFPE additive of the invention:

Solution 1: solution 1M of $LiPF_6$ in PC;
Solution 2 (Comp): solution 1M of $LiPF_6$ and 0.1N of $(C_4F_9SO_2)_2N^{(-)}Li^{(+)}$ in PC;
Solution 3: solution 1M of $LiPF_6$ and 0.1N PFPE-lithium sulphonate (EW=288) in PC.

The specific conductivity $\kappa$ values are shown in Table 5.

TABLE 5

| Solution | $\kappa$ (mS/cm) |
|---|---|
| 1 | 5.731 |
| 2 (Comp) | 5.132 |
| 3 | 5.133 |

The values show how the addition of PFPE-Li sulphonate to a conductive salt $LiPF_6$ solution, determines a small decrease of the specific conductivity, of the same order as that determined by the imide salt $(C_4F_9SO_2)_2N^{(-)}Li^{(+)}$. This Example shows that solution 2 and solution 3, respectively containing the imide salt and the PFPE-lithium sulphonate, give the same specific conductivity values.

What is claimed is:

1. Electrolytic compositions comprising a perfluoropolyether additive of formula (I):

$$T-O-(CF_2CFO)_a-(CFO)_b-(CF_2CF_2O)_c-(CF_2O)_d-(CF_2CFO)_e-(CFO)_f-T$$
$$\begin{array}{cccc} | & | & | & | \\ CF_3 & CF_3 & O & O \\ & & | & | \\ & & CF_2 & CF_2 \\ & & | & | \\ & & CF_2 & CF_2 \\ & & | & | \\ (1/n)M^{n+} & SO_3- & SO_3- \\ & & & (1/n)M^{n+} \end{array}$$

wherein:
  d, e, f are integers; a, b, c can be zero or integers; said units being statistically distributed along the chain, a+b+c+d+e+f such that the number average molecular weight ranges from 500 to 5×10$^5$, preferably from 1,000 to 50,000;
  T are end groups selected from —$CF_2X$(X=F, $CF_3$, Cl), —$C_3F_7$, —$CF(CF_3)COO^-(1/n)M^{n+}$, —$CF_2COO^-(1/n)M^{n+}$, —$CF_2C(O(1/n)M^{n+})_2CF_3$;
  $M^{n+}$ is a cation having valence n=1–4 selected from $Li^+$, $Na^+$, $K^+$, $Cs^+$, $Mg^{2+}$, $Ca^{2+}$, $Sr^{2+}$, $Ba^{2+}$, metal cations of the group IIIA such as $Al^{3+}$; transition metal cations, such as $Fe^{2+}$, $Fe^{3+}$, $Zn^{2+}$, $Ti^{4+}$, $Cu^{2+}$; tetraalkylammonium $NR_4^+$ cations, trialkylammonium $NR_3^+$ cations, wherein R is selected from H, a linear or branched when possible $C_1$–$C_4$ lower alkyl.

2. Electrolytic compositions according to claim 1, wherein $M^{n+}$ is a monovalent cation (n=1).

3. Electrolytic compositions according to claim 2, wherein M is $Li^+$.

4. Perfluoropolyether additives according to claim 3.

5. Electrolytic compositions according to claim 1, furthermore comprising:

one or more aprotic polar solvents;

a conductive salt.

6. Electrolytic compositions according to claim 5, wherein the conductive salt cation is selected from the group comprising alkaline, alkaline-earth metals, trivalent metals, tetra-alkyulammonium; the anion is selected from $PF_6^-$, $ClO_4^-$, $AsF_6^-$, $BF_4^-$, $(R_{f1}SO_2)(R_{f2}SO_2)N^-$, $R_{f'}SO_3^-$ wherein $R_{f1}$, $R_{f2}$, $R_{f'}$ are independently selected from $C_1$–$C_4$ perfluoroalkyl groups optionally containing heteroatoms.

7. Electrolytic compositions according to claim 5, wherein the aprotic polar solvents are selected from 1,2-dimethoxyethane, 1,2-diethoxyethane, 1,3-dioxolane, 2-methyl-1,3-dioxolane, 4-methyl-1,3-dioxolane, tetrahydrofuran, 2-methyltetrahydrofuran, 1,4-dioxane, N,N-dimethylformamide, dimethylsulphoxide, ester carbonates such as dimethylcarbonate, diethylcarbonate, propylene carbonate, ethylene carbonate.

8. Electrolytic compositions according to claim 7, wherein the solvents are ester carbonates.

9. Electrolytic compositions according to claim 5, wherein a concentration of conductive salt in the electrolytic solution is higher than 0.5 moles/litre.

10. Electrolytic compositions according to claim 9, wherein the concentration of conductive salt in the electrolytic solution is in the range 0.5–2 moles/litre.

11. Electrolytic compositions according to claim 1, wherein the concentration of the perfluoropolyether additive is higher than 10 meq/litre (calculated as cation $M^{n+}$).

12. Electrolytic compositions according to claim 11, wherein the concentration of the perfluoropolyether additive is in the range of 10 meq/litre–500 meq/litre.

13. Electrolytic compositions according to claim 1, wherein the ionic species are at least partially dissolved or dispersed in a matrix material.

14. Electrolytic compositions according to claim 13, wherein the matrix material is in the form of solid, liquid polymer, gel or porous membrane.

15. Electrolytic compositions according to claim 13, wherein the matrix material in the form of solid polymer is selected from polyethylenoxide, polyesters, polyacrylates, polyvinilydenfluoride, polyacrylonitrile.

16. Electrolytic compositions according to claim 13, wherein the matrix material in the form of porous solid membranes is selected from polyethylene, polypropylene having a surface tension in the range 28–35 mN/m (dyne/cm).

17. Electrolytic compositions according to claim 1, wherein the perfluoropolyether additive of formula (I) is obtainable by conversion of the fluorosulphonyl groups —$SO_2F$ into —$SO_3M$ groups carried out on the homopolymers of the monomer $CF_2=CFOCF_2CF_2SO_2F$ or on the copolymers of said monomer with perfluoroolefins.

18. Electrolytic compositions according to claim 17, wherein the perfluoroolefins are tetrafluoroethylene and/or perfluoropropene.

19. A method for improving the weattability of components of electrochemical systems comprising the preparation of the electrolytic composition of claim 1.

20. The method according to claim 19, wherein the electrochemical systems are lithium batteries.

21. Electrochemical system comprising the electrolytic compositions according to claim 1.

* * * * *